(12) United States Patent
Grey et al.

(10) Patent No.: US 6,914,673 B2
(45) Date of Patent: Jul. 5, 2005

(54) SAFETY APPARATUS FOR AN ATOMIC ABSORPTION SPECTROMETER BURNER

(75) Inventors: Ronald G Grey, Beamaris VIC (AU); Shaun C Holthouse, Yarra VIC (AU)

(73) Assignee: GBC Scientific Equipment Pty Ltd (AU)

( * ) Notice: Subject to any disclaimer, the term of this patent is extended or adjusted under 35 U.S.C. 154(b) by 164 days.

(21) Appl. No.: 10/343,338

(22) PCT Filed: Jul. 26, 2001

(86) PCT No.: PCT/AU01/00911
§ 371 (c)(1),
(2), (4) Date: Jan. 29, 2003

(87) PCT Pub. No.: WO02/14839
PCT Pub. Date: Feb. 12, 2002

(65) Prior Publication Data
US 2004/0012779 A1 Jan. 22, 2004

(30) Foreign Application Priority Data
Aug. 16, 2000 (AU) ............................................. PQ9445

(51) Int. Cl.⁷ .......................... G01N 21/31; G01N 21/72
(52) U.S. Cl. ...................................................... 356/315
(58) Field of Search ................................. 356/315, 417

(56) References Cited

U.S. PATENT DOCUMENTS

| 4,568,267 A | 2/1986 | Kendall-Tobias |
| 4,640,677 A | 2/1987 | Huber |

FOREIGN PATENT DOCUMENTS

| EP | 182258 | 5/1986 |
| SU | 1822948 | 6/1993 |

*Primary Examiner*—F. L. Evans
(74) *Attorney, Agent, or Firm*—Michael Best & Friedrich LLP

(57) ABSTRACT

A burner assembly and a gas box for an atomic absorption spectrometer are disclosed. The burner assembly has a spray chamber (12) for receiving oxygen, fuel and sample material and a burner (11) located on the spray chamber for receiving the mixture so the mixture can be ignited to produce a flame to facilitate analysis of the sample material by atomic absorption of radiation. Pressure transducer (30) is provided for measuring the pressure in the spray chamber so that the pressure is not of a predetermined level the burner can be shut off. A fuel line (29) supplies fuel to the spray chamber (12) and an airline (28) supplies air to the chamber (12). The lines (28) and (29) include flow restrictors (38) and (54) creating an accurate pressure drop thereby ensuring correct mixture of air and fuel.

24 Claims, 3 Drawing Sheets

SAFETY APPARATUS FOR AN ATOMIC ABSORPTION SPECTROMETER BURNER

FIELD OF THE INVENTION

Figure 1:
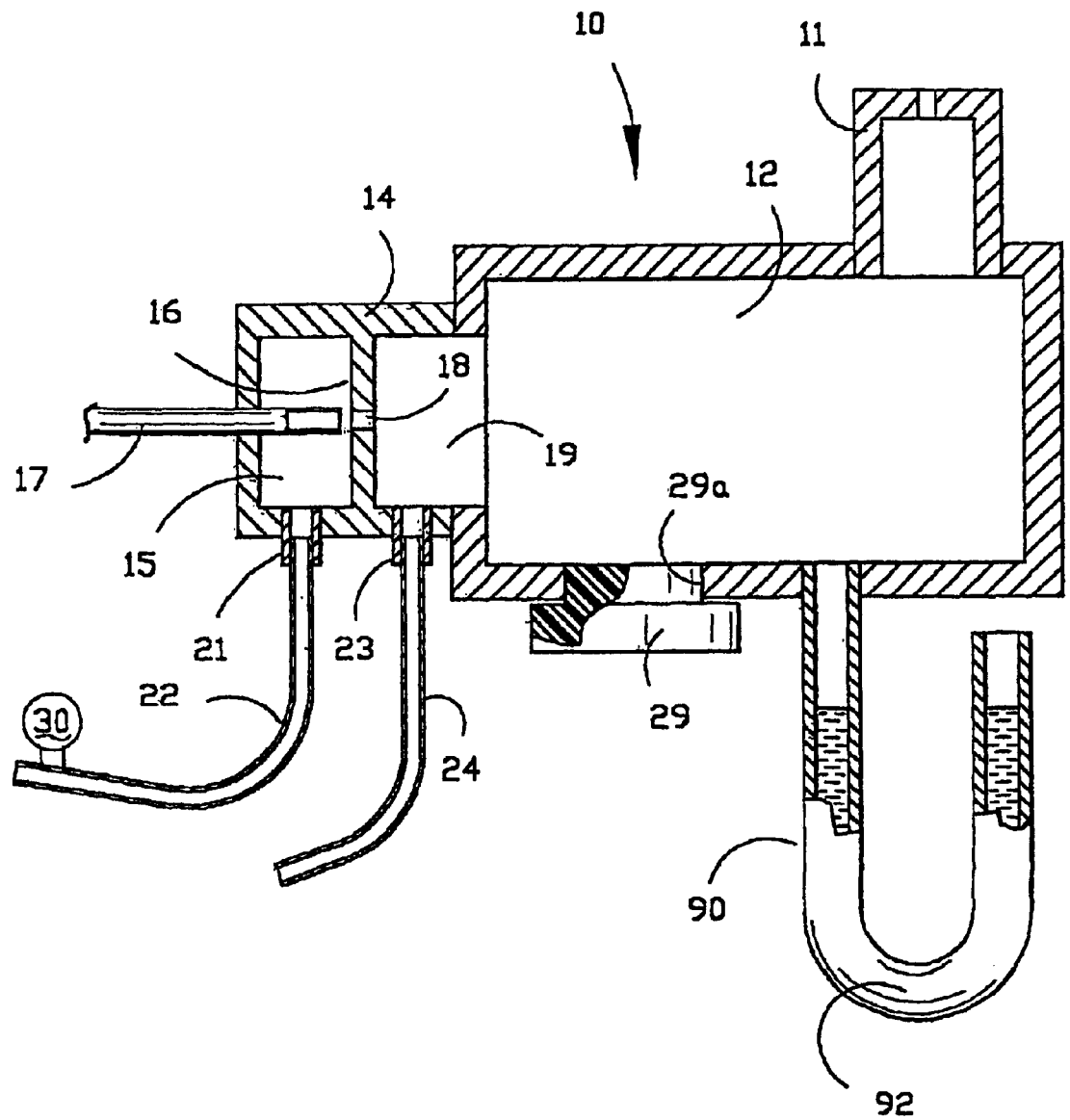

This invention relates to an atomic absorption spectrometer.

BACKGROUND OF THE INVENTION

Atomic absorption spectrometers analyse a sample by burning the sample in a flame and passing electromagnetic radiation through the flame so that the sample atoms absorb particular wavelengths of the radiation. By detecting the radiation which is absorbed by the ground state atoms in the flame the conception of the elements of interest can be determined.

In order to analyse the sample the atomic absorption spectrometer includes a burner assembly which has a spray chamber which is fluid communication with a burner. The spray chamber has a nebuliser bung which receives sample material from an inlet tube. The sample material is generally entrained in a flow of fluid. The nebuliser bung includes a baffle which has an orifice and the tube terminates adjacent the inlet to the orifice. An oxidant line communicates with the nebuliser bung on the inlet side of the orifice and a fuel and air line communicates with the nebuliser bung on the outlet side of the orifice. The bung is in fluid communication with the spray chamber so that when high pressure oxidant passes through the oxidant line, the high pressure oxidant travels through the orifice thereby creating a venturi effect within the sample tube which assists in the drawing of sample through the sample tube into the nebuliser bung and then into the spray chamber. Fuel and air supplied through the fuel line into the nebuliser bung mixes with the oxidant and sample in the spray chamber and the mixture is supplied to the burner where the fuel, air and sample are combusted in a flame for analysis.

The spray chamber has an over pressure relief device in the form of an over pressure bung which locates in an aperture in the spray chamber so that in the event of over pressure in the spray chamber the bung is forced out of the opening to relieve that pressure. An over pressure situation can occur if pressure initially drops within the spray chamber so that the flame produced by the burner can move inside the spray chamber and causes flashback. If this occurs the increase in the pressure caused by the flashback will cause the bung to be expelled from the opening thereby reducing the pressure and reducing the damage caused by the flashback.

If the bung is not located within the opening, fuel gas can leak from the spray chamber into the environment which, if the burner was to be ignited, can create an explosion.

Thus, if the spray chamber assembly components are not inserted correctly, the highly flammable gas produced by the mixture of the fuel and air may be allowed to leak into atmosphere. Such a leak can have two hazardous outcomes;

the velocity of the gasses exiting burner is reduced to well below the flame velocity causing the flash-back referred to above; and sufficient fuel gas leaks into the environment to create an explosive atmosphere if, for example, a bung is not located in the opening or incorrectly located in the opening.

Similar hazards can also arise from using the wrong burner in the assembly, or allowing the burner to become excessively clogged (from salt formations etc). For these reasons, most gas burner assembly designs rely on interlocks to guard the operator from such hazards. These interlocks are typically realised by means of micro-switches or read switches which sense the presence of components in the assembly. A typical example is a micro-switch which is activated by the presence of the over pressure relief device inserted into the spray chamber body. If the micro-switch is not activated by proper location of the over pressure relief device or bung, the instrument will not ignite the flame or vent fuel into the environment.

Burner assemblies are also provided with a liquid trap for draining off aspirated liquid which is supplied to the chamber with the sample. The liquid trap is typically in the form a u-shaped tube into which liquid can drain. The u-shaped tube forms an "s-bend" so that liquid in the s-bend acts as a plug to prevent leakage of flammable gas from the spray chamber through the liquid trap. As liquid flows into the liquid trap, the liquid can flow out of the s-bend but a sufficient amount of liquid remains in the s-bend to form a plug thereby preventing the escape of gasses from the spray chamber through the liquid trap. A magnet may be provided with floats on the surface of the liquid and when the liquid level is at a height sufficient for safe operation (indicating that the liquid plug is in place), the magnet triggers a reed switch to provide a signal indicative of the fact that the integrity of the liquid trap is in tact.

SUMMARY OF THE INVENTION

The object of a first aspect of the present invention is to improve the safety of atomic absorption spectrometers and in particular the burner assembly of such spectrometers to detect any significant leaks in the spray chamber and to improve the economy and manufacturability of the safely interlocks, and to create an assembly that can be immersed for cleaning without damaging the interlock system.

The invention, in a first aspect, may be said to reside in a burner assembly for an atomic absorption spectrometer including;

a spray chamber for receiving oxidant, fuel and sample material and allowing mixing of the oxidant, fuel and sample material;

a burner locatable on the spray chamber for receiving the mixture so that the mixture can be ignited to produce a flame to facilitate analyses of the sample material by atomic absorption of radiation; and pressure monitoring means for monitoring the pressure within the spray chamber so that if the pressure is not at a predetermined level thereby indicative of a safety risk, the burner can be shut off by shutting off supply of at least the fuel to the burner assembly.

Thus, according to this aspect of the invention the integrity of the burner assembly is monitored by measuring the pressure within the spray chamber. If the pressure changes from a predetermined expected level this will be indicative of the fact of a safety risk, such as leakage caused by failure to locate an over pressure relief device or bung or incorrect location of that device in the spray chamber, or inclusion of an incorrect burner in the burner assembly, or clogging of a burner, or other leakage from the spray chamber. In the event of one of the conditions which may otherwise cause a hazardous situation, the supply of fuel can be shut off to prevent ignition of the burner, or to shut off the burner if already ignited, so the fault can be corrected.

Preferably the burner assembly includes;

a nebuliser bung coupled to the spray chamber, the nebuliser bung having a baffle including an orifice;

a sample tube for supplying sample coupled to the nebuliser bung and terminating adjacent the orifice;

an oxidant line for supplying oxidant, connected to the nebuliser bung on the inlet side of the orifice;

a fuel line connected to the nebuliser bung on an outlet side of the orifice; and wherein the supply of oxidant through the oxidant line causes flow of the oxidant through the orifice thereby creating a venturi effect to assist in drawing of sample material through the sample tube into the nebuliser and through the orifice, and so that the oxidant, sample and fuel can mix in the spray chamber for supply to the burner.

Preferably the spray chamber includes an over pressure relief device.

Preferably the spray chamber includes a liquid trap including an s-bend portion for retaining a plug of liquid so that aspirated liquid can drain from the spray chamber through the liquid trap and the plug of liquid can form a seal in the liquid trap to prevent egress of fuel, air and sample mixture from the spray chamber.

Preferably the pressure monitoring means is coupled to the oxidant line.

Preferably the oxidant line and fuel line communicate with a gas box which includes said pressure monitoring means, said gas box further including;

an inlet supply line for the input of oxidant, a shut off valve for selectively shutting off supply of oxidant, a pressure regulator for regulating the flow of oxidant, the pressure regulator having an outlet connected to a first flow restrictor, the first flow restrictor being connected to the oxidant line; and the fuel input supply including a shut off valve, a second flow restrictor and a first flow control valve, an output of the first flow control valve being coupled to the fuel line.

Preferably the oxidant supply line is also connected to the fuel line via a second flow control valve so that the fuel line supplies a mixture of fuel and oxidant to the spray chamber.

Preferably the fuel supply line includes an igniter branch for supplying fuel to an igniter for creating a flame for lighting the burner.

Preferably the igniter branch includes a shut off valve.

Preferably a first pressure sensor is coupled across the first flow restrictor for measuring the pressure drop across the first flow restrictor.

Preferably a second pressure sensor is coupled across the second flow restrictor for measuring the pressure drop across the second flow restrictor.

The first and second pressure sensors provide an indication of the flow rate of oxidant and fuel through the oxidant supply line and the fuel supply line so that the first and second flow control valves can be controlled to provide the desired flow rate of fuel to the fuel line.

Preferably the flow restrictors comprise a length of tube through which the oxidant or fuel flows so as to reduce the pressure of the fluid as the fluid flows through the tube by skin friction on the internal surface of the tube. It has been found that using a length of tube to create the pressure drop results in very accurate pressure reduction which is required to ensure that the mixture of the oxidant and fuel supplied to the spray chamber is correct thereby enabling the establishment of a flame of the desired characteristic, or enabling the flame to be modified by accurate measurement of the pressure drop caused by the first and second flow restrictors and adjustment of the flow control valves in response the pressure drop measured by the first and second pressure sensors.

In a further aspect the invention also provides an atomic absorption spectrometer having the burner assembly described above.

A second aspect of the invention concerns the manner in which a pressure drop is created in the supply of oxidant and/or fuel to the gas burner assembly of an atomic absorption spectrometer. Conventional techniques utilise an orifice in a flow tube in order to create the pressure drop. The control of pressure drop in the supply of oxidant and/or fuel is critical in order to ensure that the burner produces a flame having the correct flame characteristics for a particular analysis. The use of an orifice does not provide sufficient accuracy in the pressure drop of the oxidant or fuel because of tolerances in the formation of the orifice having regard to the small size of the orifice which in required, and therefore conventional machines do exhibit some difficulty in providing a flame of the required characteristics in order to provide good analysis results.

A further aspect of the invention may be said to reside in a gas box for an atomic absorption spectrometer, including;

an oxidant supply line for supplying oxidant to a burner assembly;

a fuel supply line for supplying fuel to the burner assembly; and a flow restrictor in at least one of the air supply line or fuel supply line, said flow restrictor comprising a length of tubing for reducing the pressure of the oxidant or fuel by skin friction caused by the internal surface of the tube and the flow of oxidant or fuel through the tube.

The use of a length of tube of the flow restrictor and the fact that the pressure drop is created by skin friction, results in a very accurate pressure drop which can be precisely controlled and accurately determined simply the length of the tube which creates the flow restrictor. Thus, better control over the flame characteristics can be obtained in an inexpensive manner and also in a manner which is easy to implement.

Preferably both the fuel supply line and the oxidant supply include a said flow restrictor.

Preferably a pressure sensor is associates with each flow restrictor for measuring the pressure drop across the flow restrictor.

Preferably the fuel supply line and the oxidant supply include respective flow control valves and the flow control valves are controlled dependant on the pressure determined by the pressure sensor to control the supply of fuel and oxidant to the gas burner.

The present invention may also be said to reside in an atomic absorption spectrometer having a gas box as described above.

A third aspect of the invention may be said to reside in a gas box for an atomic absorption spectrometer, the gas box having;

a fuel supply line;

an oxidant supply;

a first linear solenoid valve in the fuel supply line for controlling flow of oxidant through the oxidant supply line to a gas burner assembly;

a second linear solenoid valve in the fuel supply line for controlling flow of fuel through the fuel supply line to the gas burner assembly.

Preferably the gas box includes;

an input supply for the input of oxidant, a shut off valve for selectively shutting off supply of oxidant, a pressure regulator for regulating the flow of oxidant, the pressure regulator having an outlet connected to a first flow restrictor, the first flow restrictor being connected to the oxidant line; and the fuel input supply including a shut off valve, a second flow restrictor and a first flow control valve, an output of the first flow control valve being coupled to the fuel line.

Preferably the oxidant supply line is also connected to the fuel line via a second flow control valve so that the fuel line supplies a mixture of fuel and oxidant to the nebuliser bung.

Preferably the fuel supply line includes an igniter branch for supplying fuel to an igniter for creating a flame for lighting the burner.

Preferably the igniter branch includes a shut off valve.

Preferably a first pressure sensor is coupled across the first flow restrictor for measuring the pressure drop across the first flow restrictor.

Preferably a second pressure sensor is coupled across the second flow restrictor for measuring the pressure drop across the second flow restrictor.

The present invention may also be said to reside in an atomic absorption spectrometer having a gas box as described above.

BRIEF DESCRIPTION OF THE DRAWINGS

A preferred embodiment of the invention will be described, by way of example, with reference to the accompanying drawings in which;

FIG. 1 is a cross sectional view through a gas burner assembly of an atomic absorption spectrometer according to the preferred embodiment of the invention;

FIG. 2 is a fluid circuit diagram of a gas box used with the burner assembly of FIG. 1; and FIG. 3 is a block circuit diagram showing the control of the burner assembly and gas box according to the preferred embodiment of the invention.

DESCRIPTION OF THE PREFERRED EMBODIMENTS

With reference to FIG. 1 a gas burner assembly 10 is shown which has a spray chamber 12 which, at one end, is in fluid communication with a nebuliser bung 14. The nebuliser bung 14 has a baffle 16 which includes an orifice 18. The baffle 16 divides the nebuliser bung into an inlet chamber 15 and an outlet chamber 19. The outlet chamber 19 is in free fluid communication with the spray chamber 12. A sample tube 17 for the supply of sample to the burner assembly 10 passes into the inlet chamber 15 of the bung 14 and terminates adjacent an inlet of the orifice 18. In other embodiments the tube 17 could terminate just after the outlet side of orifice 18. The chamber 15 also has a gas connector 21 which connects the chamber 15 to an oxidant line 22. The chamber 19 has a gas connector 23 which connects the chamber 19 to a fuel line 24. The fuel lines 22 and 24 connect with an oxidant inlet supply line 28 and a fuel inlet supply line 29 which are shown in FIG. 2.

A gas burner 11 is coupled to the chamber 12 for receiving oxidant, fuel and sample mixture from the spray chamber 12 and for burning the mixture so that the sample can be analysed by directing a beam of electromagnetic radiation through the flame which is detected by a detector. Sample atoms in the flame will absorb radiation and in particular wavelengths and thereby measuring the spectrum of the detected radiation enables the constituents of the sample to be determined.

A pressure relief device such as a bung 29 is located in an opening 29*a* in the spray chamber 12 so that in the event of an over pressure situation created in the spray chamber 12, such as may be caused by flash-back, the bung can be expelled from the opening 29*a* to release the pressure and minimise the damage caused by the backflash.

The spray chamber 12 has a liquid trap 90 which is in the form of an s-bend for draining liquid from the spray chamber 12 which is aspirated into the spray chamber 12 with sample material through the sample supply tubes 17. That liquid can drain through the trap 90 and from the trap 90. The trap 90 is in the form of an s-bend so that a liquid plug 92 is maintained in the s-bend so as to form a seal to prevent the egress of fuel, oxidant and sample mixture from the chamber 12.

As shown in FIG. 2, the fuel supply line 28 has a first inlet branch 31 for the supply of air and a second inlet branch 32 for the supply of nitrus-oxide. The first branch 31 has a first solenoid valve 38 and the branch 32 has a second solenoid valve 39 for selectively shutting off the supply and nitrous-oxide through the branches 31 and 32. The branches 31 and 32 are coupled to branch 33 which in is coupled to a pressure regulator 35. The pressure regulator 35 has an outlet branch 36 and an outlet branch 37. The first outlet branch 36 couples to a flow restrictor 38 which is formed by a significant length of tube (which may be the same as the branch 36) and which is coiled to occupy as little space as possible within the gas box and to be neatly retained within the gas box. The flow resistor 38 connects to a branch 39 which couples to the line 22. The branch 39 and line 22 may form a continuous piece of tube.

A pressure transducer 30 for measuring the pressure in the line 22 is connected to the line 22 so as to provide a measure of the pressure in the line 22 and therefore the pressure within the spray chamber 12. The measurement of the pressure in the spray chamber 12 is indicative of the flow of oxidant through the line 22 and provides an indication of whether the gas chamber 12 is properly interlocked.

If the integrity of the gas burner 10 is not intact such as may be caused by the bung 29 not being located in the opening 29*a* or not located correctly in the opening 29, gas and fuel mixture will escape through the opening 29*a* thereby reducing the pressure within the spray chamber 12. This reduction in pressure will be measured by the pressure transducer 30 and if the pressure is not about equal to a predetermined pressure the control processing circuitry (shown in FIG. 3 and which will be described in more detail hereinafter), can shut off flow of fuel and air to the spray chamber 12 to prevent operation of the burner 11 or, if the burner 11 is operating, shut off the burner 11.

Typical spray chamber pressures under maximum flow are set out below.

| Spray Chamber Condition | p(Pa) |
|---|---|
| Burner or Bungs missing | 70 |
| Air acet Burner-empty liquid trap | 200 |
| Air acet Burner-normal operation | 260 |
| Air acet Burner 20% clogged | 310 |
| NOX Burner-empty liquid trap | 510 |
| NOX Burner-normal operation | 675 |
| NOX Burner 20% clogged | 875 |
| Pressure drop with 3 mm diameter leak | 35 |

With an NOX burner operating normally the above table shows normal operating pressure will be 675 Pa. If the burner is an air acetylene burner the normal operating pressure within the spray chamber is 260 Pa. If the burner or bung is missing the pressure will reduce to 70 Pa and this will be measured by the transducer 30. If the air acetylene burning is in place the liquid trap is empty the pressure in the spray chamber will drop to 200 Pa. If the burner is, say 20% clogged, the pressure will increase to 310. If the NOX burner is used and the liquid trap 90 is empty the pressure will drop to 510 Pa and if the burner is 20% clogged the pressure will increase to 875 Pa. A 3 mm diameter leak in the system will reduce the pressure 235 Pa. Thus, by measuring these pressures with the transducer 30 an indication can be obtained as to a particular fault condition and the burner shut off or prevented from operating until the fault is rectified.

Figure 2:
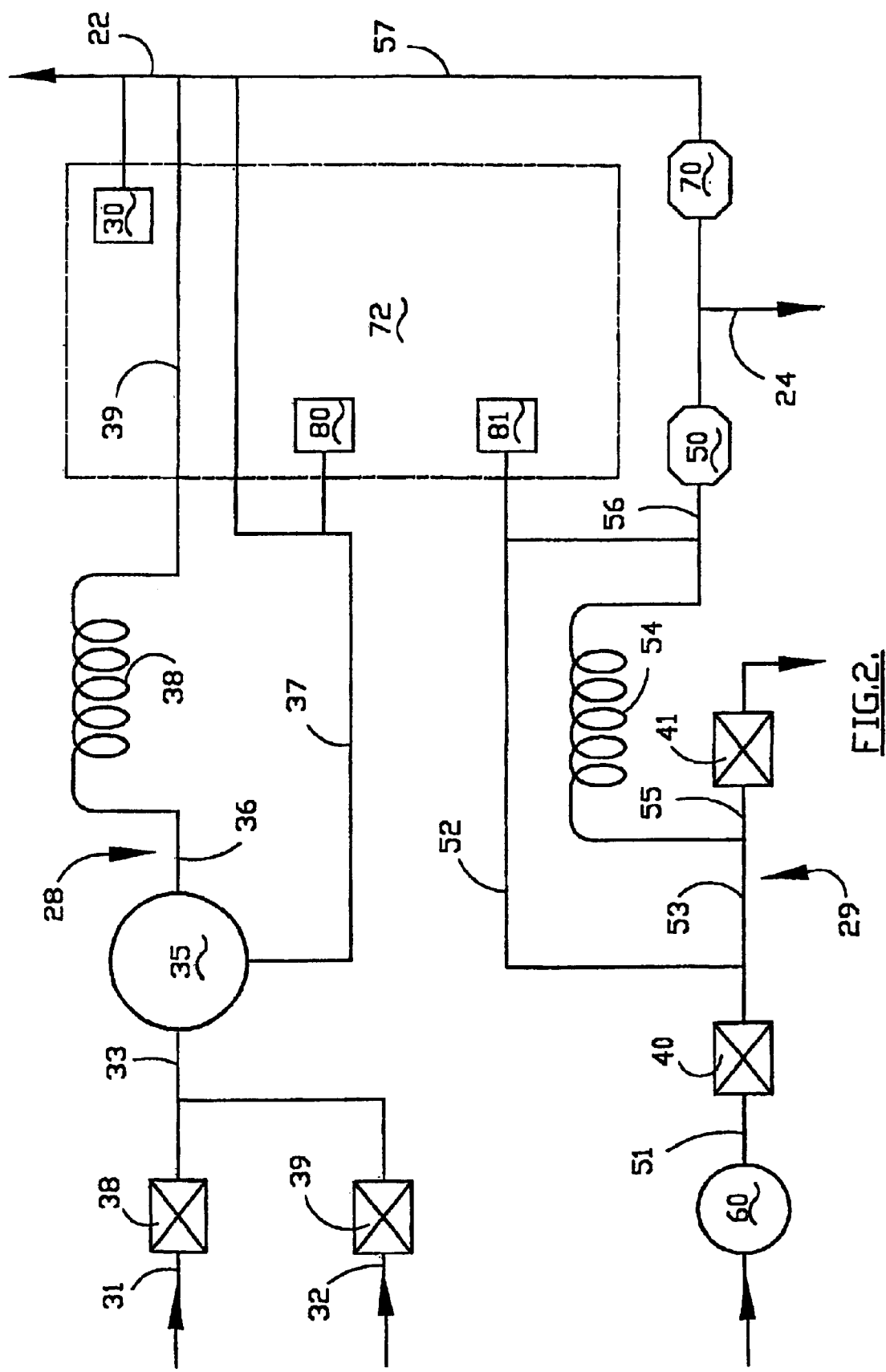

As shown in FIG. 2, the branch 37 is also connected to the supply line 22 and a pressure transducer 30 is connected in the branch line 37 for measuring the pressure drop across the flow restrictor 38.

The fuel supply line 29 includes a branch 51 which has a pressure switch 60 which measures whether sufficient fuel pressure is being supplied in the branch 51. If the pressure measured by the switch 60 is not sufficient to correctly operate the burner 11 the supply of fuel and/or air can be completely shut off as will be described in more detail with reference to FIG. 3. The branch 51 also includes a third solenoid valve 41 which has an output side connected to a branch 52. The branch 52 includes a pressure transducer 81. The output of the solenoid 40 is also connected to a branch 53 which includes a second flow restrictor 54. The branch 53 also connects to an igniter line 55 which includes a four solenoid valve 41. The igniter line 55 provides pure fuel to an igniter burner for creating a fuel flame, such as an acetylene flame, for igniting the burner 11 when required. The restrictor 54 connects to a branch 56 which includes a first flow control valve 50, the branch 52 also joins with the branch 56 so that the pressure transducer 81 is connected across the flow restrictor 54 for measuring the pressure drop across the flow restrictor 54. The branch 56 connects to fuel line 24. The oxidant supply line 29 also includes a branch 57 which connects with the branch 37 and also the oxidant line 22. The branch 57 has a second flow control valve 70 and the branch 57 also joins with the fuel line 24. Thus, the fuel supplied through the line 24 is a mixture of fuel, such as acetylene and also of oxidant such as air and nitrous-oxide.

The pressure transducers 30, 80 and 81 may be located on a control circuit board 72 which forms part of the control circuitry of the gas box shown in FIG. 2. The pressure transducer 30 is different from the pressure transducers 80 and 81 which receive inputs from each side of the respective restrictors 38 and 54 so that the pressure drop across those restrictors can be measured by the transducers 50 and 51. The pressure transducer 30 simply measures the absolute value of the pressure within the line 22 and therefore within the spray chamber 12.

When fuel and oxidant is supplied to the lines 22 and 24 the supply of oxidant through the line 22 flows through the orifice 18 and into the chamber 19 where it mixes with fuel supplied through the line 24. The flow of oxidant through the orifice 18 creates a venturi effect at the end of the supply tube 17 for facilitating the drawing of sample material through the tube 17 into the chamber 19 and then into the spray chamber 22 so that the fuel, oxidant and sample can mix in the spray chamber 22 for supply to the burner 11 for combustion by the burner 11.

When the spectrometer is initially turned on, oxidant can be supplied to the oxidant line 22 via the supply line 28 so as the pressurise the spray chamber 12. The pressure in the spray chamber 12 will be measured by the pressure transducer 30 and if the pressure is within the required predetermined range an indication of the integrity of the spray chamber 12 can be made. Thus, the operating sequence of the spectrometer may continue by supply of fuel to the fuel line 24 and ignition of the burner 11. However, if the pressure within the spray chamber 12 is outside the predetermined range, fuel will not be supplied through the line 24 and the burner 11 will not be ignited because the low pressure reading will be taken as an indication that the spray chamber 12 has not been properly interlocked and either the bung 29 is missing or not correctly located in the opening 29a, or a wrong burner 11 has been located on the spray chamber 12 or the spray chamber 12 is otherwise leaking. The burner 11 will therefore not be ignited and fuel will not be supplied through the line 24 until the fault is rectified.

If the plug 92 is not in place or, it evaporates away for some reason, the escape of gas through the trap 90 will be detected by the pressure transducer 30 because the pressure within the chamber 12 will drop. Thus, the pressure detected by the transducer 30 will be outside the predetermined range thereby cause a signal to be supplied to the micro-processor 100 which will shut off the solenoid valves 241 to prevent supply of oxidant and fuel to the chamber 12.

Figure 3:
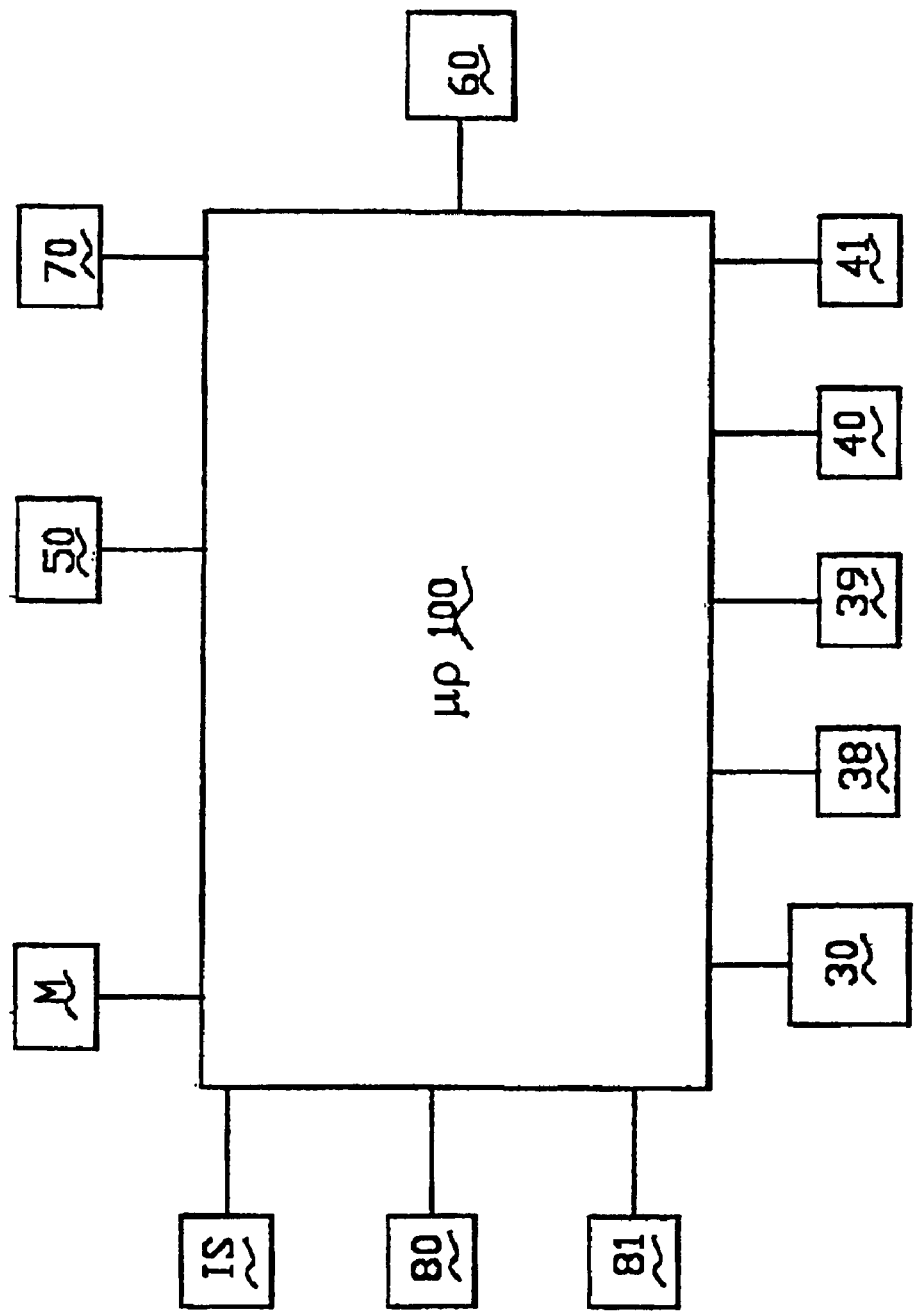

FIG. 3 is a block circuit diagram showing the control operation of the spectrometer and in particular of the gas box shown in FIG. 2. The solenoids 38 to 41 are connected to micro-processor 100 which also receives control signals from the pressure switch 60 the flow control valves 50 and 70 and the pressure transducers 80 and 81. The microprocessor 100 will initially open solenoid valves 38 and 39 for supply of oxidant through line 28 to oxidant line 22 and then to chamber 12. If the pressure transducer 30 measures that the pressure within the chamber 12 is within the predetermined range the micro-processor 100 will open solenoid valves 40 and 41 so that fuel can flow through the line 29 to the fuel line 24 so that the oxidant, fuel and sample mixture can mix in the chamber 12 for supply to the burner 11. The supply of fuel through the branch line 55 will also enable the igniter to be ignited so that the burner 11 can be ignited to produce a flame for analyses.

The pressure switch 60 will measure the flow of fuel in the branch line 51 and if the pressure of the fuel is not sufficiently high to create a stable flame then the pressure switch 60 will supply a signal to the micro-processor 100 which will cause the solenoids 38 to 41 to be shut off to stop supply of oxidant and fuel until the fault is rectified.

The pressure regulator 35 regulates the pressure supplied in the branch lines 36 and 37 so that the pressure of oxidant supplied to the line 22 and also the line 24 can be a certain pressure to produce a predetermined flow rate to produce a flame at the burner 11 of the desired characteristics. The nature of the flame 11 at the burner can be modified by the pressure of oxidant and fuel supplied through the oxidant line 22 and fuel line 24 and an indication of the supply of oxidant and fuel is made by measuring the pressure drop across the flow restrictors 38 and 54 by the transducers 80 and 81. The transducers 80 and 81 supply signals to the microprocessor 100 indicative of the pressure drop across the restrictors 38 and 54 and from that information an indication can be made as to the supply of fuel and oxidant to the chamber 12 and therefore the nature of the flame produced at the burner 11. If it is desired to modify the flame 11 the microprocessor can output signals to the first and second control valves 50 and 70 so as to control those valves to modify the amount of fuel and oxidant supplied to the fuel line 24 to inturn alter the characteristics of the flame.

Thus, the supply of the oxidant and fuel can be controlled by the flow control valves 50 and 70 which, inturn control, by measuring the pressure drop across the flow restrictors 38 and 54. The flow control valves 50 and 70 are linear solenoid valves which, as will be apparent from the above description, can control the flow of fluid into the line 24 from the branch 57 and the branch 56 between a predetermined maximum and a predetermined minimum flow rate.

The micro-processor 100 shown in FIG. 3 is also connected a mains supply sensor M for determining that main supply power is present and also to an infer-red sensor IS which detects that a flame is actually present at the burner 11. If the infer-red detector IS does not detect the flame a signal is provided to the micro-processor 100 so that supply of fuel and oxidant can be shut of by shutting of the solenoid valves 38 and 41.

The flow restrictors 38 and 54 which are in the form of a length of tube provide a pressure drop by virtue of the length of the tube involved and which is created of skin friction of the fluid passing through the tubes which form the restrictors 38 and 54. The amount of skin friction and the pressure drop which it creates is dependant on the viscosity of the fluid supplied through the restrictors 38 and 54 an since this is substantially constant, a very accurate and reliable pressure drop can be obtained by the restrictors 38 and 54 simply by making the restrictors 38 and 54 of a desired length. Since it is easy to determine the length of the tubes which will form the restrictors 38 and 54 the very accurate pressure drop can be obtained in a very simple manner because it simply requires the use of a tube to form the restrictors 38 and 54 of a required length. The required length can easily be determined and installed in the supply lines 28 and 29.

Since modifications within the spirit and scope of the invention may readily be effected by persons skilled within the art, it is to be understood that this invention is not limited to the particular embodiment described by way of example hereinabove.

The claims defining the invention are as follows:

1. A burner assembly for an atomic absorption spectrometer including;
    a spray chamber for receiving oxidant, fuel and sample material and allowing mixing of the oxidant, fuel and sample material;
    a burner locatable on the spray chamber for receiving the mixture so that the mixture can be ignited to produce a flame to facilitate analyses of the sample material by atomic absorption of radiation; and
    pressure monitoring means for monitoring the pressure within the spray chamber so that if the pressure is not at a predetermined level thereby indicative of a safety risk, the burner can be shut off by shutting off supply of at least the fuel to the burner assembly.

2. The assembly of claim 1 wherein the burner assembly includes;
    a nebuliser bung coupled to the spray chamber, the nebuliser bung having a baffle including an orifice;
    a sample tube for supplying sample coupled to the nebuliser bung and terminating adjacent the orifice;
    an oxidant line for supplying oxidant, connected to the nebuliser bung on the inlet side of the orifice;
    a fuel line connected to the nebuliser bung on an outlet side of the orifice; and
    wherein the supply of oxidant through the oxidant line causes flow of the oxidant through the orifice thereby creating a venturi effect to assist in drawing of sample material through the sample tube into the nebuliser and through the orifice, and so that the oxidant, sample and fuel can mix in the spray chamber for supply to the burner.

3. The assembly of claim 1 wherein the spray chamber includes an over pressure relief device.

4. The assembly of claim 1 wherein the spray chamber includes a liquid trap including an s-bend portion for retaining a plug of liquid so that aspirated liquid can drain from the spray chamber through the liquid trap and the plug of liquid can form a seal in the liquid trap to prevent egress of fuel, air and sample mixture from the spray chamber.

5. The assembly of claim 2 wherein the pressure monitoring means is coupled to the oxidant line.

6. The assembly of claim 2 wherein the oxidant line and fuel line communicate with a gas box which includes said pressure monitoring means, said gas box further including;
    an inlet supply line for the input of oxidant, a shut off valve for selectively shutting off supply of oxidant, a pressure regulator for regulating the flow of oxidant, the pressure regulator having an outlet connected to a first flow restrictor, the first flow restrictor being connected to the oxidant line; and
    the fuel input supply including a shut off valve, a second flow restrictor and a first flow control valve, an output of the first flow control valve being coupled to the fuel line.

7. The assembly of claim 2 wherein the oxidant supply line is also connected to the fuel line via a second flow control valve so that the fuel line supplies a mixture of fuel and oxidant to the spray chamber.

8. The assembly of claim 2 wherein the fuel supply line includes an igniter branch for supplying fuel to an igniter for creating a flame for lighting the burner.

9. The assembly of claim 8 wherein the igniter branch includes a shut off valve.

10. The assembly of claim 6 wherein a first pressure sensor is coupled across the first flow restrictor for measuring the pressure drop across the first flow restrictor.

11. The assembly of claim 6 wherein a second pressure sensor is coupled across the second flow restrictor for measuring the pressure drop across the second flow restrictor.

12. The assembly of claim 6 wherein the flow restrictors comprise a length of tube through which the oxidant or fuel flows so as to reduce the pressure of the fluid as the fluid flows through the tube by skin friction on the internal surface of the tube.

13. An atomic absorption spectrometer having a burner assembly including;
    a spray chamber for receiving oxidant, fuel and sample material and allowing mixing of the oxidant, fuel and sample material;
    a burner locatable on the spray chamber for receiving the mixture so that the mixture can be ignited to produce a flame to facilitate analyses of the sample material by atomic absorption of radiation; and
    pressure monitoring means for monitoring the pressure within the spray chamber so that if the pressure is not at a predetermined level thereby indicative of a safety risk, the burner can be shut off by shutting off supply of at least the fuel to the burner assembly.

14. The atomic absorption spectrometer of claim 13 having a gas box including;
    an oxidant supply line for supplying oxidant to the burner assembly;
    a fuel supply line for supplying fuel to the burner assembly; and
    a flow restrictor in at least one of the oxidant supply line or fuel supply line, said flow restrictor comprising a length of tubing for reducing the pressure of the oxidant or fuel by skin friction caused by the internal surface of the tube and the flow of oxidant or fuel through the tube.

15. The atomic absorption spectrometer of claim 14 wherein both the fuel supply line and the oxidant supply include a said flow restrictor.

16. The atomic absorption spectrometer of claim 14 wherein a pressure sensor is associated with each flow restrictor for measuring the pressure drop across the flow restrictor.

17. The atomic absorption spectrometer of claim 16 wherein the fuel supply line and the oxidant supply include respective flow control valves and the flow control valves are controlled dependant on the pressure determined by the pressure sensor to control the supply of fuel and oxidant to the gas burner.

18. The atomic absorption spectrometer of claim 13 having a gas box including;
   a fuel supply line;
   an oxidant supply;
   a first linear solenoid valve in the fuel supply line for controlling flow of oxidant through the oxidant supply line to the burner assembly; and
   a second linear solenoid valve in the fuel supply line for controlling flow of fuel through the fuel supply line to the burner assembly.

19. The atomic absorption spectrometer of claim 18 wherein the gas box includes;
   an input supply for the input of oxidant, a shut off valve for selectively shutting off supply of oxidant, a pressure regulator for regulating the flow of oxidant, the pressure regulator having an outlet connected to a first flow restrictor, the first flow restrictor being connected to the oxidant line; and
   the fuel input supply including a shut off valve, a second flow restrictor and a first flow control valve, an output of the first flow control valve being coupled to the fuel line.

20. The atomic absorption spectrometer of claim 18 wherein the oxidant supply line is also connected to the fuel line via a second flow control valve so that the fuel line supplies a mixture of fuel and oxidant to the burner.

21. The atomic absorption spectrometer of claim 18 wherein the fuel supply line includes an igniter branch for supplying fuel to an igniter for creating a flame for lighting the burner.

22. The atomic absorption spectrometer of claim 21 wherein the igniter branch includes a shut off valve.

23. The atomic absorption spectrometer of claim 19 wherein a first pressure sensor is coupled across the first flow restrictor for measuring the pressure drop across the first flow restrictor.

24. The atomic absorption spectrometer of claim 19 wherein a second pressure sensor is coupled across the second flow restrictor for measuring the pressure drop across the second flow restrictor.

* * * * *